United States Patent [19]
Hanson et al.

[11] Patent Number: 6,149,881
[45] Date of Patent: Nov. 21, 2000

[54] PYROLYSIS METHOD FOR INCREASING LIMONENE PRODUCTION AND NOVEL OVEN TO FACILITATE SUCH METHOD

[76] Inventors: Curtiss D. Hanson, 3921 Heritage Rd., Cedar Falls, Iowa 50613; Timothy Burrell, P.O. Box 232, Tempe, Ariz. 85280; James E. Haworth, 918 SW. Emma Ave., Des Moines, Iowa 50315; James A. Olson, 2928 Love Joy Dr., Cedar Falls, Iowa 50613

[21] Appl. No.: 09/389,822

[22] Filed: Sep. 3, 1999

Related U.S. Application Data

[62] Division of application No. 08/922,490, Sep. 3, 1997, Pat. No. 5,977,421.

[51] Int. Cl.$^7$ .............................. C10B 1/10; C10G 1/02; C10G 9/20
[52] U.S. Cl. .................. 422/203; 422/204; 422/205; 422/209; 422/167; 422/174; 422/184.1; 422/199; 202/180; 585/241
[58] Field of Search .................... 422/164, 167, 422/174, 184.1, 199, 203, 204, 205, 209; 202/180; 585/241

[56] References Cited

U.S. PATENT DOCUMENTS

| | | | |
|---|---|---|---|
| 4,084,521 | 4/1978 | Herbold et al. | 110/242 |
| 4,214,110 | 7/1980 | Moroe et al. | 585/241 |
| 4,229,185 | 10/1980 | Sass | 48/197 |
| 4,308,103 | 12/1981 | Rotter | 202/117 |
| 4,740,270 | 4/1988 | Roy | 201/35 |
| 4,849,057 | 7/1989 | Steinstrasser et al. | 202/96 |
| 5,087,436 | 2/1992 | Roy | 423/461 |
| 5,099,086 | 3/1992 | Roy | 585/1 |
| 5,229,099 | 7/1993 | Roy | 423/461 |
| 5,464,503 | 11/1995 | Avetisian et al. | 20/3 |
| 5,720,232 | 2/1998 | Meador | 110/346 |

*Primary Examiner*—Bekir L. Yildirim
*Attorney, Agent, or Firm*—Andrus, Sceales, Starke & Sawall, LLP

[57] ABSTRACT

The amount of limonene produced during pyrolysis of scrap tire carcass or polyisoprene rubber can be increased by decreasing residence time of the isoprene gas produced during the thermal degradation of polyisoprene rubber in the high temperature reactor region of an oven. This is achieved by using a novel oven design which permits rapid expansion of the isoprene gas away from the high temperature reactor region of the oven to a cooler region where the gas forms limonene and condenses. This pyrolysis method also decreases the amount of soot produced while increasing the amount of limonene produced. Furthermore, this system readily enables separation of the solid, liquid and gas phases produced during pyrolysis.

9 Claims, 2 Drawing Sheets

PYROLYSIS METHOD FOR INCREASING LIMONENE PRODUCTION AND NOVEL OVEN TO FACILITATE SUCH METHOD

CROSS-REFERENCE TO RELATED APPLICATIONS

This application is a division of application Ser. No. 08/922,490, filed Sep. 3, 1997, now U.S. Pat. No. 5,977,421.

BACKGROUND OF THE INVENTION

Estimates of the generation of scrap tires produced in the United States are on the order of 2 million tons per year. Although these tires contain a high percentage of useful hydrocarbons, high grade steel and carbon black, approximately 70% are disposed of in landfill sites, open dumps, or stockpiled. This results in serious environmental problems as well as the loss of potential economic value. Because tires do not degrade, they are not good candidates for landfills, and open dumping may result in accidental fires which produce high pollution emissions. Other common fates of scrap tires include shredding for combustion or as an additive to road asphalt. While these approaches provide a simple method of waste reduction, air emission concerns are inherent and optimal recovery of the energy and chemical components are not obtained.

Recently, pyrolytic recycling of scrap tire, i.e. thermal decomposition in the absence of $O_2$, is receiving renewed interest because of its ability to produce hydrocarbon oils that can be used as fuel additives. These hydrocarbons typically have high energy content on the order of 40–50 MJ/kg (1700 BTU/lb). 20 In addition, this process also permits the recovery of the high grade steel typically used in tires as well as carbon in the form of smokeless fuel, carbon black, or activated charcoal.

A recent evaluation of pyrolytic recycling of scrap tires indicates that it can be an economically viable process if marketable products can be efficiently collected. Due to the economic and environmental attraction, a number of bench-scale and pilot studies for tire pyrolysis have been recently reported.

These systems typically use inert atmospheres and decompose the rubber at temperatures ranging from 700°–900° C. Under these conditions, the maximum collectable yield of the hydrocarbon product is only 30% of the tire mass. However, when the temperature is decreased to 500°–700° C., the yield of hydrocarbon oil is increased to 40–50% of the tire mass. Although the reduction of temperature permits both a savings in the process energy required and an increase in the amount of condensible hydrocarbons, low temperature pyrolysis also produces a viscous mixture of high molecular weight carbon compounds ($C_{10}$–$C_{20}$) having a high C:H ratio (e.g. creosote and polycyclic aromatic hydrocarbons), also known as soot. Unfortunately, these compounds reduce the effectiveness of the pyrolysis resulting in poor thermal degradation of the rubber and making product reclamation difficult, if not impossible. In addition, the difficulty in removing these hydrocarbons often leads to the build up of combustible materials in pyrolysis ovens. Another drawback to these compounds is that they are not easily recyclable.

One material of interest that is produced in high quantities during the pyrolytic decomposition of tires is limonene. Limonene has many extremely fast growing industrial applications. It is used in the formulation of industrial solvents, resins, adhesives and as a dispersing agent for pigments. It is also used as a feed stock for the production of fragrances and flavorings. Limonene is biodegradable, a natural solvent, environmentally safe with excellent solvency, rinsability and high wetting penetration and detergent properties. It has been used in a wide range of applications including water-based degreasers, natural lemon-scented all-purpose cleaners, hand cleaners and replacements for chlorofluorocarbon solvents to clean electronic circuit boards.

SUMMARY OF THE INVENTION

A pyrolysis method that increases the amount of limonene produced compared to conventional pyrolysis techniques from scrap tire carcasses or polyisoprene rubber. This is achieved via minimizing residence time of the isoprene gas produced during the thermal degradation of the polyisoprene rubber in the high temperature region of an oven. By allowing isoprene gases to expand freely into a low energy environment, dimerization results and isoprene readily converts to limonene.

In accordance with one aspect of the invention, a method of increasing the production of limonene from the pyrolysis of polyisoprene rubber, comprises the steps of pyrolytically decomposing polyisoprene rubber to produce isoprene gases in an oven having a relatively high temperature reactor region and relatively low temperature condensation region; minimizing residence time of said isoprene gases in the relatively high temperature reactor region of said oven; condensing said isoprene gases so that isoprene gases dimerize to limonene; and collecting said limonene.

This invention also relates to a new oven which facilitates decreasing residence time of isoprene gases in the high temperature region of the oven thereby increasing limonene production. This is achieved by using a novel oven, which permits rapid condensation of isoprene gases to occur and therefore decreases the amount of undesirable soot and environmentally hazardous byproducts produced. Furthermore, this type of system allows simple separation of the three phases produced during pyrolysis.

In accordance with this aspect of the invention, an oven for pyrolyzing polyisoprene rubber to produce limonene, comprises a housing defining a high temperature reaction region for pyrolyzing polyisoprene rubber and a low temperature condensation region wherein isoprene gases produced as a result of pyrolyzing the isoprene rubber dimerize to limonene; a support for holding polyisoprene rubber to be pyrolyzed in the high temperature reaction region; heating means for heating said reaction region to a pyrolyzing temperature; cooling means for cooling said low temperature condensation region to an isoprene condensation temperature; and means for enhancing the transfer of the isoprene gases from said high temperature reaction region to said low temperature condensation region.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
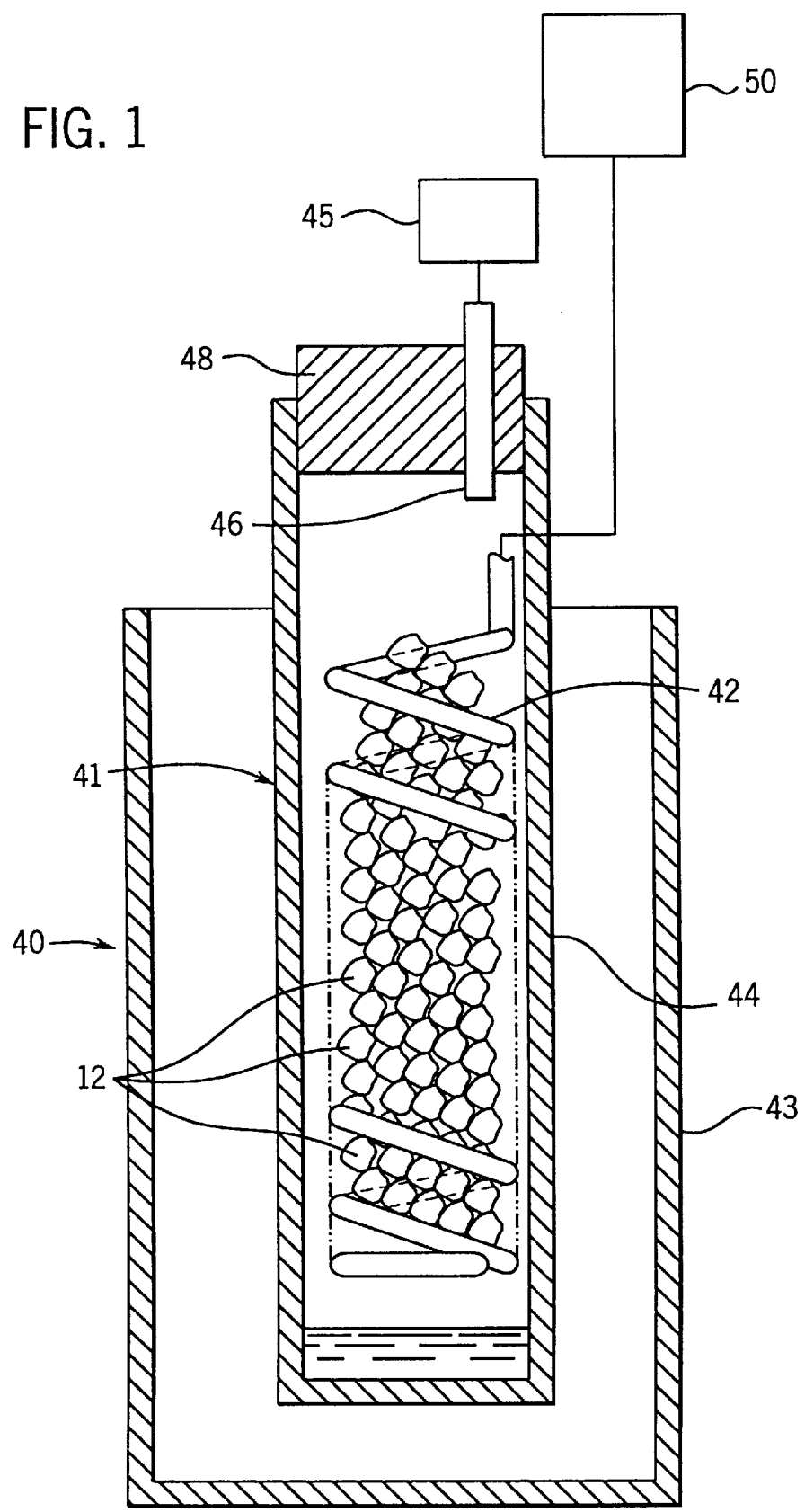
FIG. 1 is a schematic cross-sectional view of a first embodiment of the novel pyrolysis oven of the present invention.

During preliminary experiments, a conventional small tube furnace was used to thermally decompose a sample of scrap tire to determine the distribution of liquids, solids and gases formed during the pyrolysis process. It was determined that pyrolysis at 396° C. gives three phases. First, a solid phase which represents 38% in weight of the pyrolysis products, essentially constituted of activated carbon. Second, a liquid phase which represents 60% of the bulk product. Finally, the gaseous phase, which represents only 2% of the bulk. This phase comprises the likely precursors for the gas-phase reactions leading to the products found in the liquid phase, which are of primary interest.

This liquid hydrocarbon mixture was analyzed by gas chromatography/mass spectrometry (GC-MS) and contained a mixture of $C_8$–$C_{10}$ isomers, including limonene. Results from the GC-MS analysis of the liquid fraction of pyrolysis product obtained are found in Table 1 below. The mixture consists of a complicated distribution of many products, largely, aliphatic $C_8$–$C_{10}$ isomers. Limonene, which has a molecular weight of 136, is the major product of vacuum pyrolysis which comprises of approximately 50% of the total liquid product distribution as a result of the dimerization of isoprene. The other half of the distribution is comprised of unsaturated hydrocarbons and aromatic compounds (i.e. compounds with a high C:H ratio) such as cyclohexene, toluene and ethyl benzene. These later compounds are similar to the soot compounds produced during the combustion or open burning process.

TABLE 1

| Peak # | R Time | Name | Emp. Frm | % |
|---|---|---|---|---|
| 186 | 3:10 | Cyclohexene | $C_6H_{10}$ | 15 |
| 215 | 3:58 | 3-Methyl-1-Cyclohexene | $C_7H_{12}$ | 2 |
| 225 | 3:75 | Toluene | $C_7H_8$ | 6 |
| 278 | 4:63 | 1,3-Cycloctadiene | $C_8H_{12}$ | 3 |
| 306 | 5:10 | Ethylbenzene | $C_8H_{10}$ | 3 |
| 315 | 5:25 | Xylene | $C_8H_{10}$ | 2 |
| 342 | 5:70 | Sryrene | $C_8H_8$ | 8 |
| 446 | 7:43 | Camphene | $C_{10}H_{16}$ | 2 |
| 486 | 8:10 | M-Methylstyrene | $C_9H_{10}$ | 2 |
| 565 | 9:42 | 1,2-Dimethyl-3-Ethylbenzene | $C_{10}H_{14}$ | 4 |
| 575 | 9:58 | Limonene | $C_{10}H_{16}$ | 51 |
| 692 | 11:53 | Terpinolene | $C_{10}H_{16}$ | 2 |

The structure of limonene produced by this process is as follows:

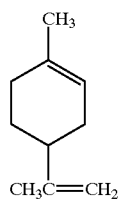

Limonene is a monoterpene produced from two isoprene units, the isoprene structure of which is as follows:

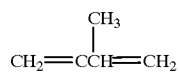

It was determined that the product distribution formed during pyrolysis could be modeled using Fourier transform ion cyclotron resonance mass spectroscopy (FT-ICR). FI-ICR provides an excellent analytical technique which gives quantitative and qualitative information regarding gas-phase ion/molecule reaction pathways. By modeling the products formed during the gas-phase reactions, via FT-ICR mass spectrometry, the initial impact spectrum of the pyrolysis products was determined. In the resulting mass spectrum, five important peaks were observed: $C_3H_3$+(m/z=39), $C_3H_5$+(m/z=41), $C_3H_8$+(m/z=44). Although (m/z=44) could indicate $CO_2$ or $C_2H_4O$, it seems improbable because pyrolysis is thermal decomposition in the absence of oxygen. Furthermore, isolation of m/z=44 produces a hydrocarbon series which is inconsistent with the former compounds. In addition, $C_4H_8$+(m/z=56) and $C_5H_7$+(m/z=67) resulting from $C_5H_8$ by loss of a proton were observed. At a reaction time of five seconds, extinction of ions having m/z=44 and appearance of $C_5H_9$+(m/z=69), $C_6H_9$+(m/z=81), $C_7HI$+(m/z=95) and $C_8HI_3$+(m/z=109) was observed. These peaks correspond to low molecular weight unsaturated hydrocarbons found in a liquid fraction. It is important to note that the good correlation between the products formed from the gas-phase reactions of isoprene compared to the pyrolysis products indicates that the pyrolysis reactions can be effectively modeled.

The results of these modeling experiments indicated that two energy dependent reaction mechanisms exist. One being a radical cation mechanism and the other a low energy diamerization mechanism. As seen in Scheme 1, the polyisoprene rubber thermally decomposes by a-Bscission mechanism to form the individual isoprene subunits in the gas phase. Under low temperature conditions these individual isoprene subunits can dimerize to form the low C:H compound, limonene. However, under more energetic conditions, i.e. high temperature conditions, the isoprene subunits can fragment and react by either ion-molecule or neutral free radical mechanisms to form cyclohexene and the other undesirable hydrocarbons found in the liquid-fraction product distribution. During pyrolysis, both of these mechanisms occur. However, they occur at different rates at the different respective temperatures depending on the location and resident time of the gases within the high temperature reactor region of the oven where the temperature is between 400° C. to 800° C., preferably between 500° C. to 700° C. The low energy or condensation regions typically occur in the cooler regions at the extremes of the oven where the temperature is below 200° C. and preferably between 100° C. to 150° C. The high energy reactions occur when the gases formed during pyrolysis have long residence times in the high energy regions of the oven. These results suggest that once isoprene is produced by the thermal degradation of the polyisoprene rubber, it expands throughout the oven. In other words, the isoprene which is constrained within the high temperature regions of the oven will produce the unwanted cyclic, aromatic and polycyclic compounds found in the liquid fraction. This decomposition produces the individual isoprene units. At this point, individual isoprene molecules are in the gas-phase free to react. As temperature increases, the high energy reactions start to predominate over the low energy reactions and soot is produced at a higher rate. As the temperature increases more, the limonene that is being produced or has been produced, starts to decompose or undergoes a reverse Diels-Alder reaction and reverts back into its original isoprene units. Under these conditions soot becomes the predominate product. Ovens which constrict the expansion of gases and, therefore, increase the residence time within the high temperature region will thus selectively produce soot-like compounds having low C:H ratios.

These results indicate that oxygen from the steam environment have been incorporated into the liquid products by gas-phase reactions occurring in the oven. Since the cyclohexene fraction has been reduced by this addition, it is clear that it is a product of the high energy gas-phase reactions.

It is important to note that the amount of limonene produced utilizing a steam environment was unchanged by the addition of steam suggesting that the limonene is not a

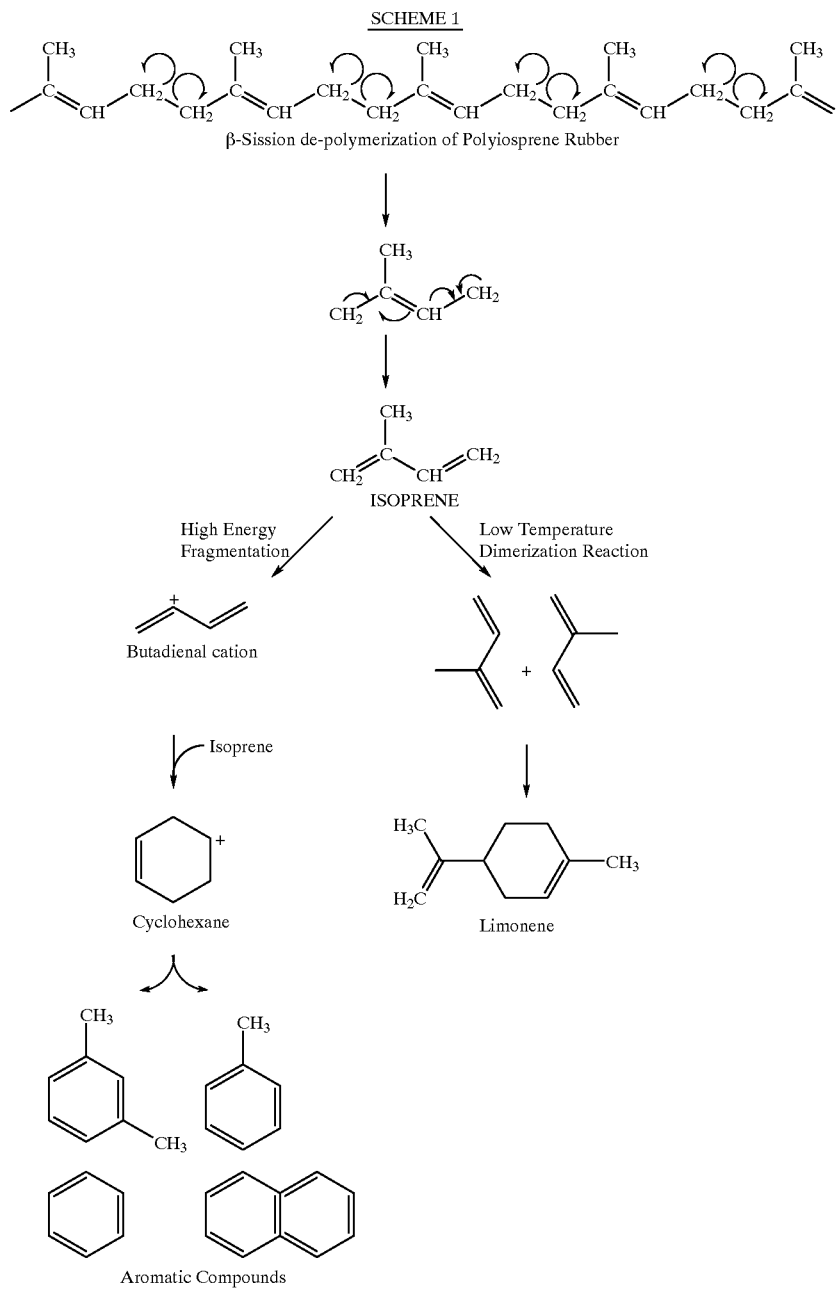

Thus, the concept of high energy fragmentation forming aromatics was tested by introducing a steam environment into the reactor oven during pyrolysis. The liquid fraction was collected and analyzed by GC-MS. It is clear from the results of this analysis that the amount of cyclohexene produced during pyrolysis has been significantly reduced and a new compound containing oxygen has been produced.

product of high energy gas-phase reactions and must be produced by a different mechanism. It was found that the isoprene which migrates to the lower energy areas of the oven due to less constriction forms limonene. Isoprene which quickly expands from the high temperature reactor region out into a cooler region of the pyrolysis apparatus actually dimerizes to form the limonene found in the liquid fraction. Therefore, if an apparatus is constructed to provide rapid removal of the isoprene produced during pyrolysis to a cooler condensation region, the amount of limonene produced will be increased resulting in a more economically viable process.

To address this issue a perforated reactor tube design was developed to permit the rapid transference of the gaseous isoprene into a cooler region where dimerization to form limonene can occur. Finally, a perforated reactor tube design permits the separation of the three phases produced during pyrolysis. In particular, a perforated reactor tube permits instant separation of the solid and liquid fractions produced by expansion of the condensable hydrocarbons into the two different regions of the oven.

EXAMPLE 1

Apparatus: To test the concept that a greater constriction and higher energy environment produces a variety of aromatics and that lower constriction and lower energy environment produces increased amounts of limonene, an open coil oven 40 was constructed (see FIG. 1). Oven 40 is comprised of a reactor unit 41 and a cooling jacket 43. The reactor unit 41 consisted of a heater coil 42 located in a cylindrical housing 44. In this embodiment, heating coil 42 not only supports the tire pieces 12 but also is used to heat the tire pieces 12 to a pyrolyzing temperature so that no external furnace is required. The heating coil 42 is preferably made of nichrome wire which is wound in a spiral-like orientation with a ½" diameter, ⅛" space between each winding and was approximately 5" in length. Furthermore, the heater coil 42 was insulated with Sauereisen ceramic paste to reduce any effects of the nichrome on the ensuing chemistry. The heating coil 42 is heated by an energy source able to heat the coil above 400° C. Specifically, the heating coil 42 was heated by a Fisher variable 120 V auto transformer (variac) 50 and the temperature was monitored using a n/p thermocouple. A lid 48 closes the open upper end of housing 44. A vacuum is created within housing 44 by a vacuum pump 45 via line 46. Pump 45 is preferably a Welch 1.5 amp vacuum pump. Cooling jacket 43 surrounds housing 44 and may contain a coolant such as liquid nitrogen or ice to ensure all resulting gaseous products are condensed. Thus, unit 41 defines a high temperature reaction region for pyrolyzing polyisoprene rubber which is located within coil 42, and a relatively low temperature condensation region for dimerizing isoprene gases to limonene which is located between coil 42 and housing 44. Lid 48 provides for a vacuum seal and can be of any suitable material which provides for such a seal, such as rubber.

Procedure: Six 10 gram samples of scrap tire pieces (60–70 grams total) were loaded into the reactor unit 41 and the temperature was brought up to approximately 250° C. Thereafter the temperature was ramped at a constant rate up to approximately 425° C., and from this point, the tire pieces 12 were allowed to decompose for 5 minutes. After 5 minutes, the variac was turned off and the liquid was collected.

Liquid Sample Preparation: The liquid portions retrieved from the reactors was cleaned as follows:

First, a small amount of methylene chloride was added to the liquid samples to extract both polar and non-polar components. This solution was placed in a separatory funnel and agitated. The organic layer was separated from the inorganic and polar organic layers. The organic sample was filtered to remove any solid particulate from the sample using a 50 ml buret filled with 100–200 mesh type 60 A special Mallinckradt silicar silica gel. The sample was loaded on the buret and washed using additional methylene chloride. The resultant filtrate was rotovaped to remove the excess solvent. These oils were then added to either methylene chloride or trichlorotrifloroethane solvents for the gas chromatographic/mass spectrometry analysis.

GC/MS conditions: Gas chromatographic/mass spectrographic analysis (GC/MS) was performed on a Finnigan MAT ITD 800 GC/MS and associated vacuum system controlled by an IBM compatible PC 386. A 30 meter DB5 phase column with a 0.25 mm I.D. was used in the chromatographic separation. The temperatures of the injection and detection ports were both 250° C. with Helium carrier gas.

The mass spectra were recorded at an ionizing energy of 70 eV. Mass spectral data and chromatographic peak areas were determined using the integrated data system. Identification of the compounds was performed using a NIST library and confirmed by interpretation of the fragmentation data. Gas-Phase Reactions: Gas-phase reaction experiments were performed on an IonSpec OMEGA 50 Fourier transformed ion cyclotron resonance mass spectrometer (FT-ICR) which a high field Walker Scientific electromagnet held at 1.03 Tesla, background pressures of $8.5 \times 10^{-10}$ torr were maintained in the vacuum system analyzing chamber by a Blazers 330 liter/second turbomolecular pump backed by an Alcatel direct drive roughing pump. Gaseous reagents were set and maintained using a Varian leak valve. Experimental pressures ranging from $2 \times 10^{-7}$ to $3 \times 10^{-7}$ torr in a 5 cubic centimeter analyzer cell were measured using a Bayard-Alpert type ionization gauge. The gaseous samples were ionized by electron impact from a 20 millisecond electron beam at an electron energy of 60–70 eV. The filament current ranged from 1.2 to 1.6 υA. Data were collected using the Ion Spec OMEGA 50 data system.

Results and Discussion: It is important to note that under liquid nitrogen conditions, only one peak is observed at a retention time (r.t.) of 410 (with the exception of the methylene chloride peak at r.t. 150). The percentage yield of limonene based on this approach has an observed increase of greater than 90%. The elimination of all other components in the mixture is consistent with a selective production of limonene by reducing the residence time of the evolved gases. This approach reduces the high temperature reactions and therefore reduces any unwanted side products.

A second trial was performed using an ice water coolant as a replacement for the liquid nitrogen. These results are consistent with the initial data confirming the selective production of limonene with a low cost cooling system.

EXAMPLE 2

Figure 2:
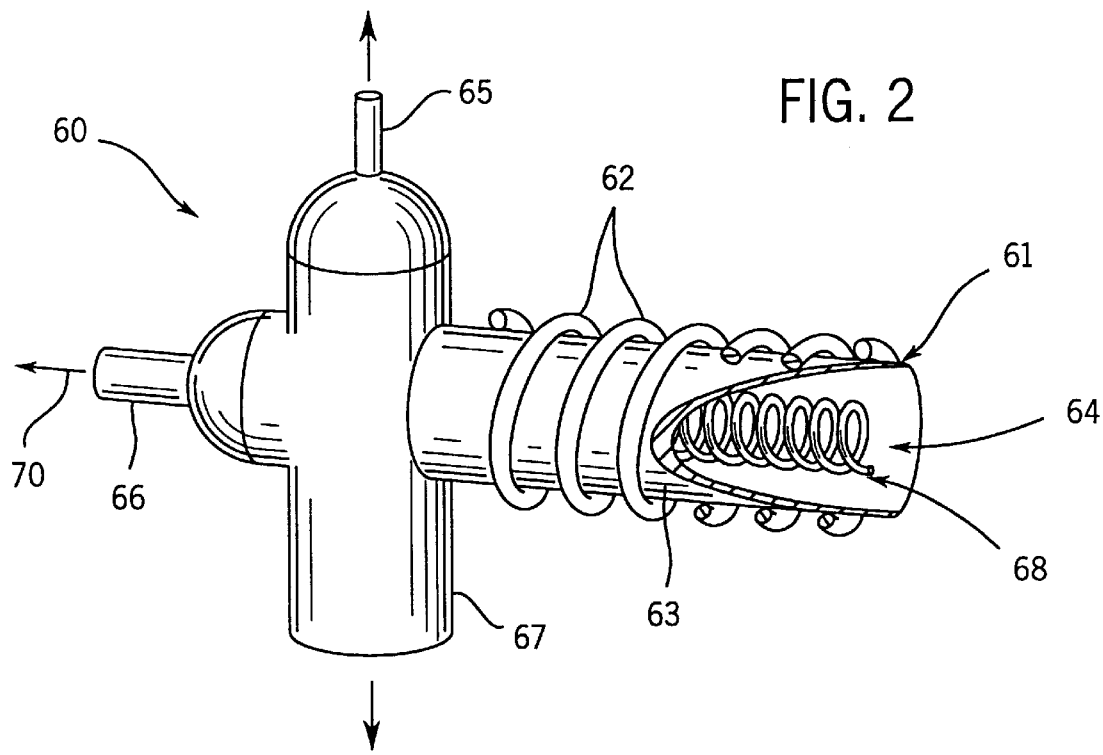
FIG. 2 is a schematic perspective view of a second embodiment of the novel pyrolysis oven of the present invention.
Figure 3:
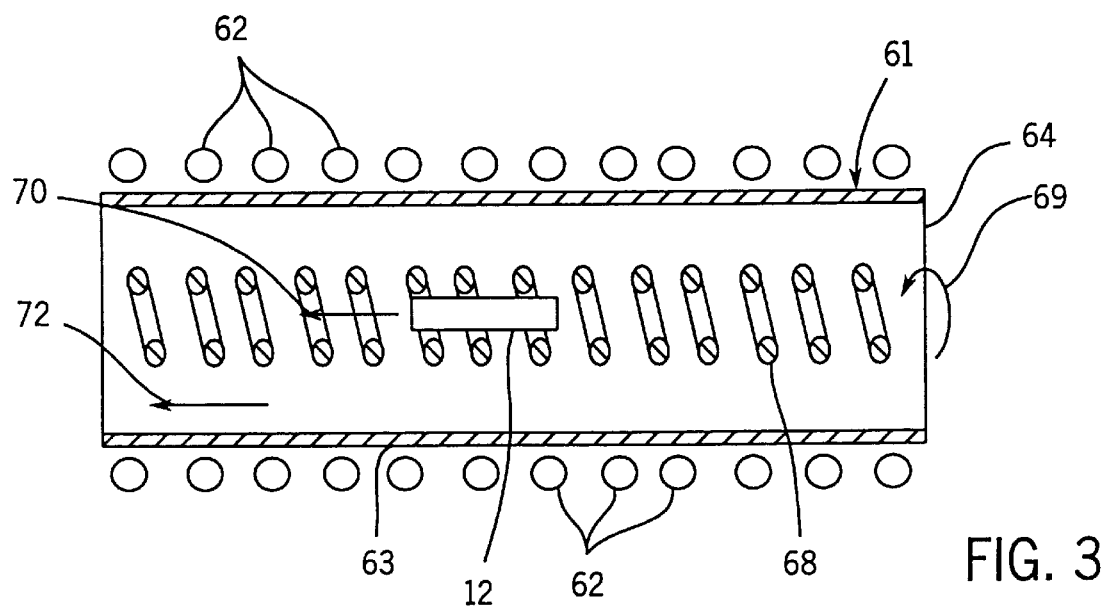
FIG. 3 is a schematic cross-sectional view of a portion of the oven illustrated in FIG. 2.

Apparatus: To illustrate the concept that a continuous process, rather than a batch process is described in Example 1, may be developed, a second embodiment of a pyrolyzing oven 60 is shown in FIGS. 2 and 3. Oven 60 is comprised of a reactor unit 61 and cooling cools 62. Reactor unit 61 includes a cylindrical housing 63 having an inlet 64 for feeding tire pieces 12, an outlet 65 for collecting off gases, an outlet 66 for solids collection, and a third outlet 67 for liquid collection. A heater coil 68 is coaxially mounted therein. As in Example 2, coil 68 not only supports tire pieces 12 but also is used to heat the tire pieces 12 to a pyrolyzing temperature. In this embodiment, however, coil 68 is rotated in the direction of arrow 69 by any conventional means to move tire pieces 12 downstream in the direction of arrow 70 from inlet 64 to outlet 66. Cooling coils 62 surround housing 63 and contain a coolant such as ice water or liquid nitrogen to create a low temperature condensation region between coil 68 and housing 63, especially adjacent the interior surface of housing 63. As shown best in FIG. 3, the individual windings of coil 68 are spaced from one another i.e. are "vented" to allow for the free and rapid expansion of gases created during pyrolysis within coil 68 in the high temperature central reaction region of housing 63. These gases, once condensed, also move downstream in the direction of arrow 72 to be eventually collected via outlet 67 where limonene can be separated and collected.

That which is claimed:

1. An oven for pyrolyzing polyisoprene rubber to produce limonene, comprising:

a housing defining a high temperature reaction region for pyrolyzing polyisoprene rubber and a low temperature condensation region wherein isoprene gases produced as a result of pyrolyzing said polyisoprene rubber dimerize to limonene;

a support for holding said polyisoprene rubber to be pyrolyzed in said high temperature reaction region;

heating means for heating said reaction region to a pyrolyzing temperature;

cooling means for cooling said low temperature condensation region to an isoprene condensation temperature wherein said cooling means comprises a cooling coil or a cooling jacket surrounding said housing and a coolant disposed in said means; and transfer means for enhancing the transfer of the isoprene gases from said high temperature reaction region to said low temperature condensation region.

2. The oven of claim 1 wherein said housing comprises a cylinder and said reaction region is disposed coaxially therein.

3. The oven of claim 2 wherein said support comprises a coil located within said cylinder.

4. The oven of claim 3 wherein said transfer means comprises spaces between windings of said coil.

5. The oven of claim 3 wherein said heating means comprises a source of electric current, and said coil comprises a heater coil.

6. The oven of claim 1 wherein said cooling means comprises a cooling jacket surrounding said housing, and a coolant disposed in said jacket.

7. The oven of claim 1 wherein said cooling means comprises a cooling coil surrounding said housing, and a coolant disposed in said cooling coil.

8. The oven of claim 1 wherein said housing includes an inlet for feeding rubber to said reaction region; a first outlet for collecting condensed liquid, a second outlet for collecting gases, and a third outlet for collecting solids.

9. The oven of claim 3 further including drive means for rotating said coil to move rubber through said reaction chamber.

* * * * *